US00PP25278P2

(12) United States Plant Patent
Jones

(10) Patent No.: US PP25,278 P2
(45) Date of Patent: Feb. 3, 2015

(54) ***LEUCANTHEMUM* PLANT NAMED 'LDDWH02-2'**

(50) Latin Name: ***Leucanthemum* hybrid**
Varietal Denomination: LDDWH02-2

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 123 days.

(21) Appl. No.: 13/815,233

(22) Filed: Feb. 11, 2013

(51) Int. Cl.
*A01H 5/00* (2006.01)

(52) U.S. Cl.
USPC ..... Plt./286

(58) Field of Classification Search
USPC ..... Plt./263.1, 286, 294
See application file for complete search history.

*Primary Examiner* — Kent L Bell
(74) *Attorney, Agent, or Firm* — Cassandra Bright

(57) ABSTRACT

A new and distinct *Leucanthemum* hybrid cultivar named 'LDDWH02-2' is disclosed, characterized by late flowering, a compact plant form and strong branching which produces higher quantities of cuttings per plant. The new variety is a Leucanthemum hybrid, and naturally blooms from Spring to Fall.

3 Drawing Sheets

Figure 1:
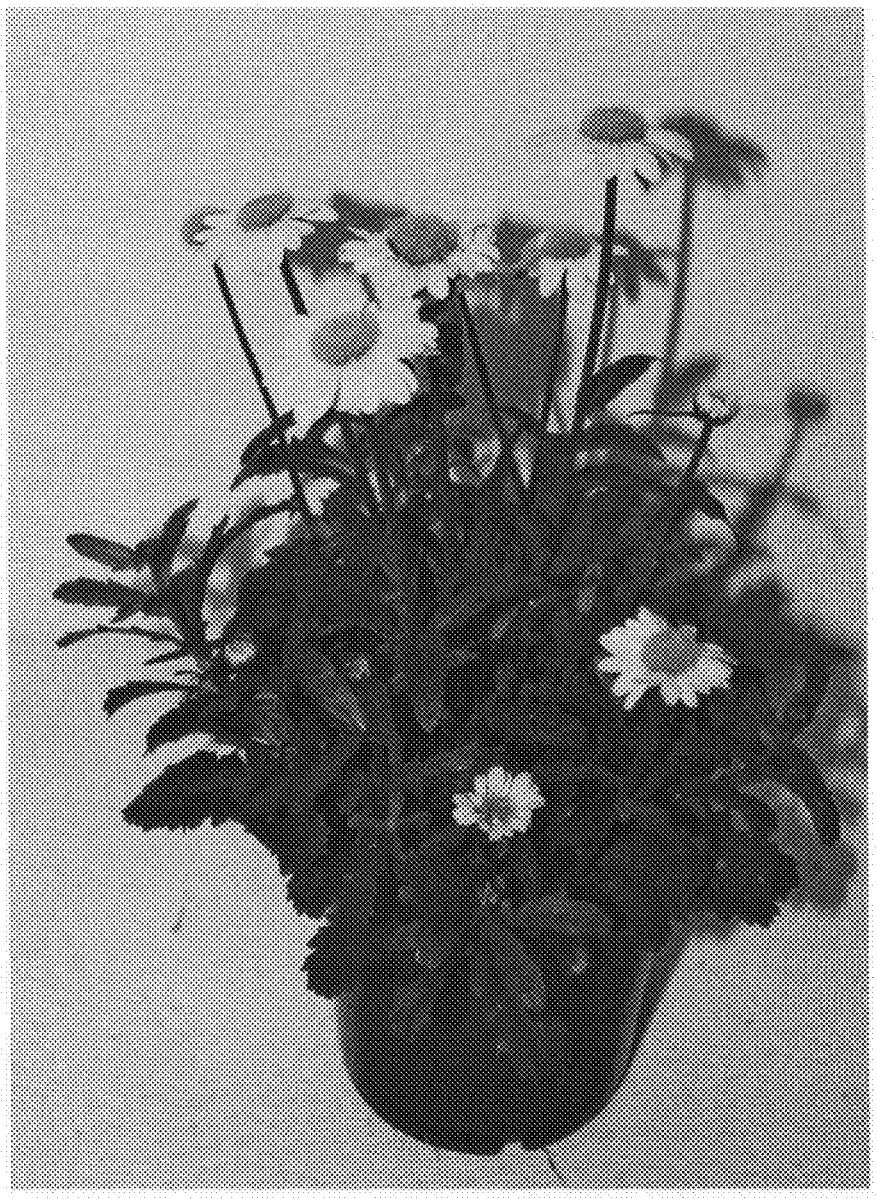

Latin name of the genus and species: *Leucanthemum* hybrid.
Variety denomination: 'LDDWH02-2'.

BACKGROUND OF THE INVENTION

The new cultivar was discovered as a spontaneous, naturally occurring whole plant mutation by the inventor, Steve Jones. The parent variety is the unpatented, variety *Leucanthemum* hybrid 'Kiemar' U.S. Plant Pat. No. 12,978. The new variety was discovered Fall of 2011, by the inventor in a commercial planting of *Leucanthemum* hybrid 'Kiemar' in Santa Paul, Calif. The inventor noticed one plant among more than 100 plants of the parent variety growing with a different plant habit and beginning to flower later than the other plants.

Asexual reproduction of the new cultivar 'LDDWH02-2' by vegetative cuttings was first performed in the Fall of 2011, at a commercial greenhouse in Santa Paula, Calif. The inventor noted that plants of the new variety consistently produced more branches, and more vegetative cuttings than the parent variety. All subsequent propagation has shown that the unique features of this cultivar are stable and reproduced true to type in successive generations

SUMMARY OF THE INVENTION

The cultivar has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LDDWH02-2' These characteristics in combination distinguish 'LDDWH02-2' as a new and distinct *Leucanthemum* cultivar:

1. Late flowering, beginning to flower after approximately 8 weeks of planting.
2. Improved branching.
3. Greater production of vegetative cuttings due to better branching.
4. Compact plant growth.

PARENT COMPARISON

Plants of the new cultivar 'LDDWH02-2' are similar to plants of the parent variety, in most horticultural characteristics, however, plants of 'LDDWH02-2' are shorter, flower later and produce more lateral branches than the parent.

COMMERCIAL COMPARISON

Plants of the new cultivar 'LDDWH02-2' are similar to plants of the commercial variety *Leucanthemum* 'Angel,' U.S. Plant Pat. No. 14,289 in most horticultural characteristics. However, plants of the new cultivar 'LDDWH02-2' differ in the following characteristics;

1. 'LDDWH02-2' has a single daisy flower form, whereas 'Angel' has a somewhat anemone type flower.
2. 'LDDWH02-2' flowers 4 weeks later on average than 'Angel'.
3. Plants of 'LDDWH02-2' are shorter than plants of 'Angel'.

Plants of the new cultivar 'LDDWH02-2' are also similar to plants of the commercial variety *Leucanthemum* 'LWMWH03-0' U.S. Plant Pat. No. 23,151 in most horticultural characteristics. However, plants of the new cultivar 'LDDWH02-2' differ in the following characteristics;

1. 'LDDWH02-2' flowers approximately 3 weeks later than 'LWMWH03-0'.
2. Plants of 'LDDWH02-2' are shorter than plants of 'LWMWH03-0'.
3. Plants of 'LDDWH02-2' produce more lateral branches than plants of 'LWMWH03-0'.

BRIEF DESCRIPTION OF THE PHOTOGRAPHS

The accompanying photograph in FIG. 1 illustrates in full color a typical plant of 'LDDWH02-2' grown in a greenhouse. The pot size is a commercial 4 inch container. The plant shown is approximately 12 weeks old.

Figure 2:
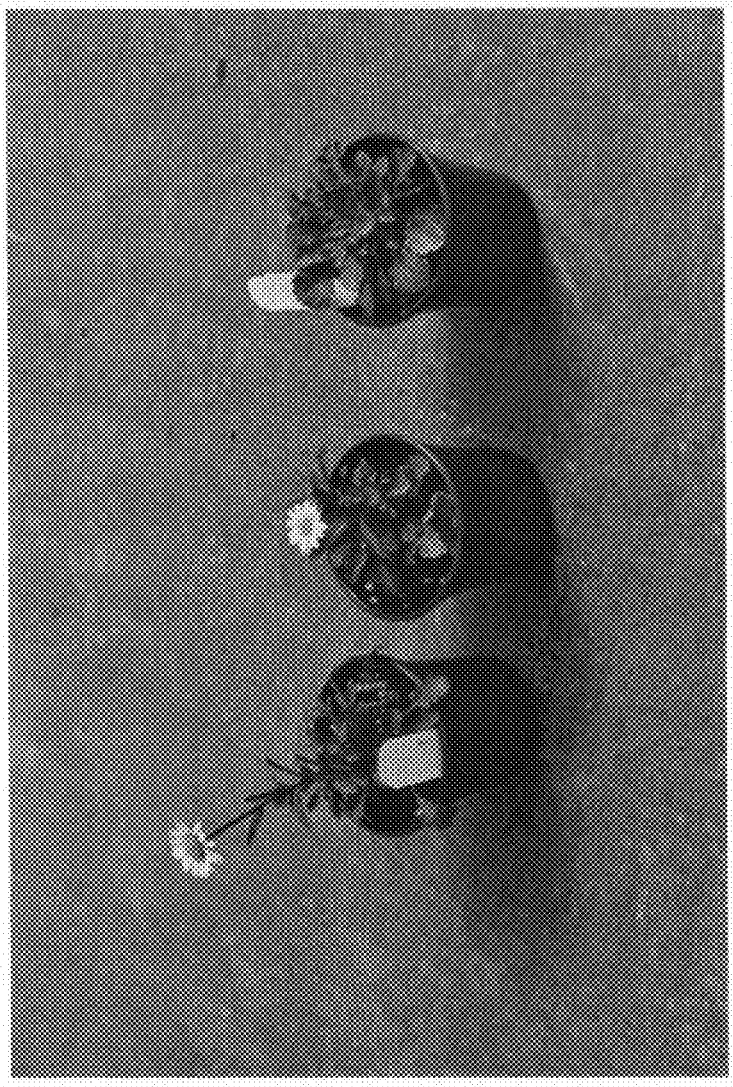

FIG. 2 illustrates a comparison of 3 different *Leucanthemum* varieties, planted at the same time and grown under identical conditions. The plant on the left is the parent variety. The plant on the right is 'LDDWH02-2'. The photograph was taken in September of 2012. The new variety has not yet begun to flower, and is instead forming a plant which will ultimately have more lateral branches.

Figure 3:
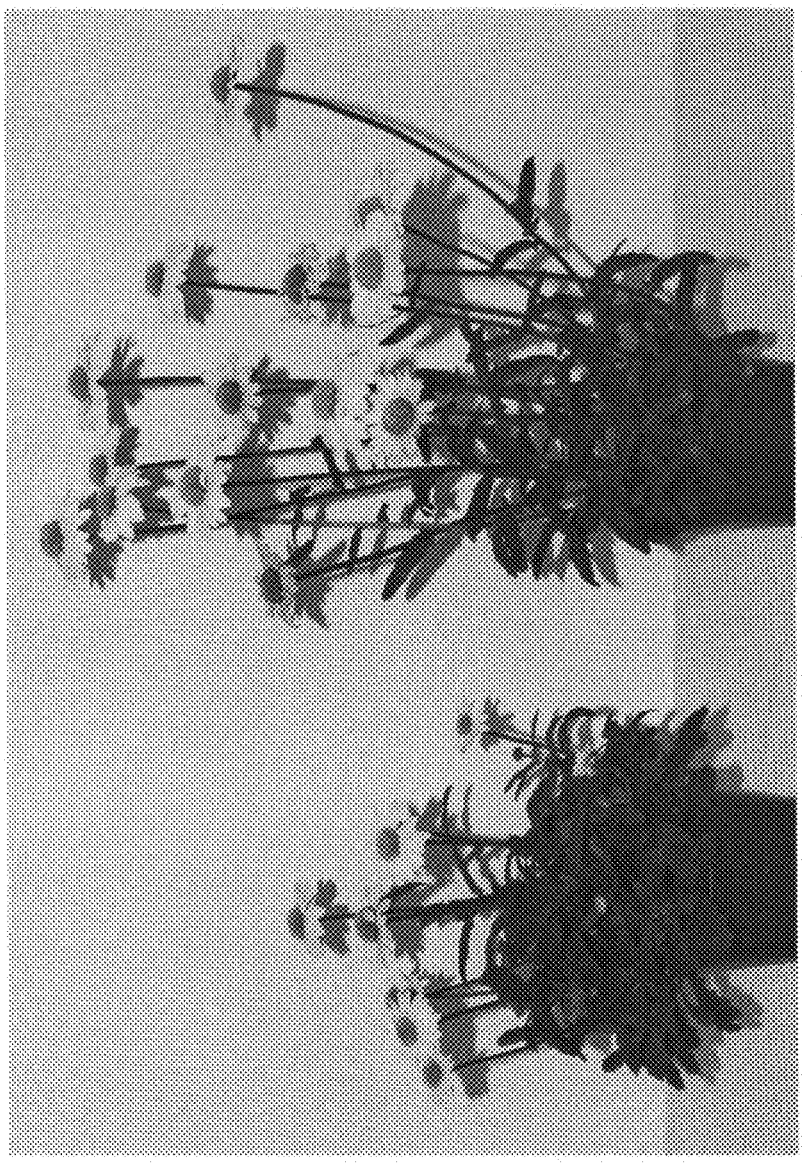

FIG. 3 illustrates a comparison with the parent variety. Plants in FIG. 3 are approximately 12 weeks old, both in full flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'LDDWH02-2' plants grown in a greenhouse in Santa Paula, Calif. from August to October. The growing temperature ranged from 15° C. to 16° C. at night to 15° C. to 32° C. during the day. Measurements and numerical values represent averages of typical flowering types.

Botanical classification: *Leucanthemum* hybrid 'LDDWH02-2'.

PROPAGATION

Time to rooting: Approximately 20 days at approximately 20° C.

Root description: Fine, fibrous.

PLANT

Height: Approximately 12 cm to top of foliar plane. Approximately 20 cm to top of the highest flower.

Blooming period: Naturally blooming Spring to early Fall.

Plant spread: Approximately 20 cm.

Growth rate: Moderate to vigorous.

Branching characteristics: Moderately free branching.

Length of lateral branches: Approximately 10 cm.

Diameter of lateral branches: Approximately 0.3 cm.

Quantity of lateral branches: Approximately 15.

Texture of lateral branches: Nonpubescent, ridged stem.

Color of lateral branches: Near RHS Green 137B.

Aspect: Straight.

Internode length: Approximately 1.0 cm.

Average number of leaves per lateral branch: Approximately 8.

Age of plant described: Approximately 10 weeks from an unrooted cutting.

FOLIAGE

Leaf:

- *Arrangement*.—Alternate, simple.
- *Average length*.—Approximately 5.3 cm.
- *Average width*.—Approximately 1.7 cm.
- *Shape of blade*.—Mature leaves spatulate, young foliage oblanceoate.
- *Apex*.—Acute.
- *Base*.—Attenuate.
- *Attachment*.—Sessile.
- *Margin*.—Dentate.
- *Texture of top surface*.—Smooth.
- *Texture of bottom surface*.—Smooth.
- *Leaf internode length*.—Approximately 3.0 cm.
- *Color*.—Young foliage upper side: Near Green 137A. Young foliage under side: Near Green 137B. Mature foliage upper side: Near Green 139A. Mature foliage under side: Near Green 137B.
- *Venation*.—Type: Pinnate. Venation color upper side: Near Yellow-Green 144B. Venation color under side: Near Yellow-Green 144C.

FLOWER

Bloom period: Naturally blooming from Spring to early Fall.

Bud:

- *Bud shape*.—Flattened sphere.
- *Bud length*.—Approximately 0.6 cm.
- *Bud diameter*.—Approximately 0.9 cm.
- *Bud color*.—Near Green 137A.

Inflorescence:

- *Quantity per plant*.—Average range around 12 to 18 open inflorescence on a mature plant.
- *Form*.—Single composite type daisy. Occurring mainly on upright terminal peduncles. Infrequently occurring on lateral peduncles.
- *Lastingness of inflorescence*.—Approximately 8 to 10 days in good condition, from fully opened.

Inflorescence:

- *Diameter of entire inflorescence*.—Approximately 4.5 cm.
- *Depth of inflorescence*.—Approximately 1.9 cm.
- *Width of disc*.—Approximately 1.3 cm.
- *Depth of disc*.—Approximately 0.7 cm.

Receptacle:

- *Width*.—0.7 cm.
- *Depth*.—0.4 cm.
- *Color*.—Near R.H.S. Yellow-Green 145C.

Ray florets:

- *Number of ray florets*.—Avg. 30, in 2 to 3 rows.
- *Length*.—Approximately 1.7 cm.
- *Width*.—Approximately 0.7 cm.
- *Apex*.—2 obtuse lobes.
- *Base*.—Attenuate.
- *Shape*.—Oblanceolate to nearly spatulate.
- *Margin*.—Entire.
- *Texture*.—Smooth.
- *Aspect*.—Flat, reflexing downward very slightly with age.

Color:

- *Ray florets*.—Upper surface at first opening: Near White 155C, minute base triangular section colored Yellow-Green 144C. Upper surface at maturity: Near White 155C base triangular section colored Green 143C. Upper surface at fading: Near White 155D. Under surface at first opening: Near White N155B minute base triangular section colored Yellow-Green 144C. Under surface at maturity: Near White 155C base triangular section colored Yellow-Green 144B. Under surface at fading: Near White 155D.
- *Disc florets*.—Number of Disc Florets.: 200. Length: Approximately 0.4 cm. Width: Approximately 0.08 cm. Apex: Blunt rounded, maturing to 5 pointed acute when flower fully opened. Shape: Cylindric. Margin:

Entire. At first opening: Near Green-Yellow 1A. At maturity: Near Yellow 9A. At fading: Near Yellow 12B.

Fragrance: Very faint.

Involucral bracts/phyllaries:

*Number*.—Approximately 40.

*Length*.—Approximately 0.4 cm.

*Width*.—Approximately 0.2 cm.

*Shape*.—Narrow deltate.

*Apex*.—Acute.

*Base*.—Truncate.

*Margin*.—Entire, membraneous.

*Texture*.—Glabrous.

*Color*.—Inside involucral bract color near R.H.S. Green 137C, with margin colored Greyed-Purple 187A and outside involucral bract color near R.H.S. Green 137C with margin colored Brown 200A.

Peduncle:

*Length*.—Average 6.8 cm.

*Width*.—Approximately 0.3 cm.

*Texture*.—Ridged.

*Color*.—Near R.H.S. Green 138A.

REPRODUCTIVE ORGANS

Androecium: Present on disc florets only.

*Stamens*.—4.

*Anther length*.—Approximately 0.03 cm.

*Anther color*.—Near Yellow 12A.

*Pollen color*.—Pollen not observed.

Gynoecium: Present on ray and disc florets.

Ray florets:

*Number of pistils per flower*.—1.

*Stigma shape*.—Two parted.

*Stigma color*.—Near Yellow 13B.

*Style color*.—Near Yellow-Green 1D.

*Style length*.—Approximately 0.2 cm.

Disc florets:

*Number of pistils per flower*.—1.

*Stigma shape*.—Two parted.

*Stigma color*.—Near Yellow 7A.

*Style color*.—Near Yellow 2D.

*Style length*.—Approximately 0.3 cm.

OTHER CHARACTERISTICS

Disease and pest resistance: Neither resistance nor susceptibility to diseases or pests has been observed in this variety to date.

Temperature tolerance: Hardy perennial. Hardy to at least −2° C., high temperature tolerance to at least 35° C.

Fruit/seed production: Fruit and seed production have not been observed in the new cultivar.

What is claimed:

1. A new and distinct cultivar of *Leucanthemum* plant named ‘LDDWH02-2’ as herein illustrated and described.

* * * * *